United States Patent [19]
Thorne

[11] Patent Number: 5,552,294
[45] Date of Patent: Sep. 3, 1996

[54] RAPID DETECTION OF VIRULENCE-ASSOCIATED FACTORS

[75] Inventor: Grace M. Thorne, Framingham, Mass.

[73] Assignee: Children's Medical Center Corporation, Boston, Mass.

[21] Appl. No.: 279,832

[22] Filed: Jul. 25, 1994

Related U.S. Application Data

[63] Continuation of Ser. No. 963,724, Oct. 20, 1992, abandoned.

[51] Int. Cl.$^6$ .................. G01N 33/569; G01N 33/543; G01N 33/62; G01N 33/573
[52] U.S. Cl. .................. 435/7.32; 435/7.35; 435/7.37; 435/7.4; 435/7.92; 435/962; 436/530; 436/177; 436/825
[58] Field of Search .................. 435/7.32, 7.35, 435/7.37, 7.4, 34, 38, 849, 962, 975, 7.92; 436/530, 547, 176, 177, 21, 825, 826

[56] References Cited

U.S. PATENT DOCUMENTS

| | | | |
|---|---|---|---|
| 4,677,080 | 6/1987 | Finkelstein et al. | 435/7.37 |
| 5,164,298 | 11/1992 | Lingwood et al. | 435/7.37 |

OTHER PUBLICATIONS

Specification Sheet for EDT-20 Received from Sigma Chemical Company.
Carl Baron and T. E. Thompson, *Biochimica et Biophysica Acta*, 382 (1975) 276–285.
J. Michael Janda, *Clinical Microbiology Reviews*, Oct. 1991, pp. 397–410 vol. 4, No. 4.
Zhen–Hai Qu et al., *Journal of Clinical Microbiology*, Apr. 1991, pp. 773–777 vol. 29, No. 4.
Ronald A. Dixon and Ian Chopra, *Antimicrobial Agents and Chemotherapy*, May 1986, vol. 29, No. 5, pp. 781–788.
Shai Ashkenazi and Thomas G. Cleary, *Journal of Clinical Microbiology*, Jun. 1989, vol. 27, No. 6, pp. 1145–1150.
David W. K. Acheson et al., *The Journal of Infectious Diseases* 1990, 161:134–137.
Thomas Larry Hale, *Microbiological Reviews*, Jun. 1991, vol. 55, No. 2, pp. 206–224.
Frances Pouch Downes et al., *Journal of Clinical Microbiology*, Jun. 1989, vol. 27, No. 6, pp. 1292–1297.
M. Basta et al., *Journal of Clinical Microbiology*, Jul. 1989, vol. 27, No. 7, pp. 1617–1622.
Pierce ImmunoTechnology Catalog and Handbook, vol. I, 1990 Pierce Chemical Co. USA.
Law et al., *J. Med. Microbiol.* 36:198–202, 1992.
International Encyclopedia of Pharmacology and Therapeutics, Section 119, Pharmacology of Bacterial Toxins, Chapter 13 "Shigella Toxins Description and Role in Diahrrea and Dysentery" Pergamon Press (1986) p. 243.
Brochure from New Horizons Diagnostic – SMART ™ Test.
Speirs et al, Aug. 1991, Detection of *Escherichia coli* cytotoxins by enzyme–linked immunsorbent assays. Can. J. Microbiol. 37: 650–53.
Ashkenazi et al, 1990. A method for detecting Shiga toxin and Shiga–like toxin –I in pure and mixed cultures J. Med Microbiol 32: 255–61.
Petric et al, 1987. Purification and biological properties of *Escherichia coli* verocytotoxin, FEMS Microbiol. Lett, 41: 63–8.
Panigrahi et al, 1987, Evaluation of immuno–dot–blot assay for detection of cholera–related enterotox in antigen in *Salmonella typhimurium*, J. Clin Microbiol. 25: 702–05.
Tijssen, 1985, *Practice and Theory of Enzyne Immunoassays*. Elsevier, Amsterdam. pp. 314–318.
Jawetz et al, 1982. *Review of Medical Microbiology*. Zange Medical Publications, Los Altos. p. 137.

*Primary Examiner*—Christina Y. Chan
*Assistant Examiner*—James L. Grun
*Attorney, Agent, or Firm*—Thomas J. Engellenner; Elizabeth A. Hanley; Lahive & Cockfield

[57] ABSTRACT

A method for detecting at least one virulence-associated factor (VAF), e.g., a bacterial toxin, in a sample is described. The sample suspected of containing the VAF-producing bacteria is contacted with a VAF releasing solution under conditions which release VAF from the bacteria. The released VAF subsequently is immunochemically detected. The preferred method is a membrane-based enzyme linked immunosorbent assay for immunochemically detecting the well-characterized Shiga family toxins including SLT I and SLT II. Also described is the VAF releasing solution and a kit containing the reagents for conducting the described methods.

21 Claims, 1 Drawing Sheet

RAPID DETECTION OF VIRULENCE-ASSOCIATED FACTORS

This application is a continuation of application Ser. No. 07/963,724, filed on Oct. 20, 1992, now abandoned.

TECHNICAL FIELD

This invention relates to methods for detecting bacterial factors associated with virulence in samples, such as biological specimens and food products. The invention further relates to reagents and devices used to conduct immunoassays for such factors.

BACKGROUND OF THE INVENTION

Virulence-associated factors are molecules involved in the virulence or pathogenicity of bacteria. Such factors are often associated for example, with gastrointestinal infections. Bacterial toxins are common virulence-associated factors.

Shiga toxin is the most well known member of a family of cytotoxins called "Shiga-like" toxins which are known virulence-associated factors. Shiga toxin is a multimeric protein toxin which is a potent inhibitor of eukaryotic protein synthesis. The toxin has one 32,000-mw polypeptide (the A chain) and five copies of a 7,600-mw polypeptide (the B chain). It is believed that the A chain is responsible for the toxin's ability to inhibit eukaryotic protein synthesis and the B chain is the receptor-binding moiety. The B chain recognizes cell-surface glycolipids having a terminal $\alpha$-D-Galp-(1-4)-D-Galp portion (Acheson et al., *The Journal of Infectious Diseases* 1990:161:134–137). These toxins have been found in a variety of bacteria including *E. coli*, *Vibrio cholerae*, *Shigella dysenteriae* and other species of Shigella.

Shiga-like toxins I and II (hereinafter SLT I and SLT II) have been well characterized. It has been reported that SLT I differs from Shiga toxin by one amino acid in the A chain. It further has been reported that the enzymatic activity and binding specificity of Shiga toxin and SLT I are identical (Acheson et al., cited supra; Stockbrine et al., *Infect Immun.* 1986:53:135–140). SLT II, however, has been shown to differ in primary sequence from Shiga toxin and has only 56% amino acid homology . SLT II and Shiga toxin also share the same enzymatic activity and binding affinity for cell-surface glycolipids (Acheson et al., cited supra; Jackson et al., *FEMS Microbiol. Lett* 1987; 44:109–114).

SLT-producing *E. coli* (most frequently *E. coli* serotype 0157:H7) has been implicated in the pathogenesis of diarrhea, hemorrhagic colitis, hemolytic uremic syndrome (HUS) and thrombotic thrombocytopenic purpura (TTP). HUS may result in microangiopathic hemolytic anemia, thrombocytopenia, and/or acute renal failure. HUS is the most common cause of acute renal failure in children. It has a 5–10% mortality rate in children and causes persistent disability in one third of patients. The case definition of TTP differs from HUS through the inclusion of fever and neurologic complications. The SLT-producing *E. coli* recently have emerged as the human pathogen associated with outbreaks of bloody diarrhea as well as cases of HUS and TTP in North America and Europe. The most common type of HUS develops in children following a diarrhea prodrome which is often bloody. SLT-producing *E. coli* including 0157:H7 are the most common pathogens found in such cases.

The infecting organisms have been found primarily in cattle (particularly dairy cows), milk, and meat products. *E. coli* 0157 was first recognized in food products provided by fast-food hamburger chains. The organisms appear to be highly infectious as documented in studies of outbreaks occuring in day care, nursing homes, school, and other institutional settings.

The majority of SLT producing *E. coli* strains are indistinguishable from *E. coli* in the normal fecal flora. A routine stool culture, therefore, does not detect this group of pathogens. The most predominant strain, *E. coli*. 0157:H7, ferments sorbitol slowly or not at all and therefore can be detected on special sorbitol-containing MacConkey agar medium. The sorbitol-negative colonies can be tested serologically using antisera to 0157 lipopolysaccharide and H7 flagellar antigens. Following isolation and identification of this serotype, the strains can be tested with the 4-methylumbelliferyl-$\beta$-D-glucuronide (MUG) test, another biochemical test, which has shown good correlation with toxin production. The strain is tested for production of SLT by enzyme-linked immunosorbent assay (ELISA), DNA probe or immunoblot technology to confirm pathogenicity. Presently, strains are sent to the Center of Disease Control for toxin confirmation testing.

If an individual is suspected of being infected by *E. coli* producing SLT I or SLT II, it is desirable to test stool specimens at the earliest stage possible because the chance of successful culture and isolation of this pathogen decreases with time. Although the 0157 serotype can be detected by biochemical and immunological testing in the laboratory, over 50 other serotypes, known to produce toxin, now go undetected. The specialized tests described above, ELISA, DNA probe and immunoblot are carried out only in a handful of research facilities. Tissue culture assays have been proposed, however, such testing requires antisera against the toxins to demonstrate specific neutralization, and up to four days to detect the specific toxin reaction on the cells. These assays are expensive, tedious and labor intensive. The tissue culture assays require specialized facilities, equipment and reagents and, therefore, are not desirable for routine testing purposes.

SLT-neutralizing antibodies also are demonstrable during infection by SLT producing *E. coli*. A fourfold increase in titer has been demonstrated but a serologic test directed towards the antibodies has, to date, demonstrated only low sensitivity. Serologic tests directed towards these antibodies may be appropriate for epidemiologic investigations of outbreaks or to verify recent infection in HUS or TTP patients if the infecting organism or toxin were not found in the stool, but presently available serologic testing is not sensitive enough to be an efficient routine diagnostic test.

The detection of bacterial toxins such as Shiga-like toxins is challenging because the toxins have to be released from the bacteria prior to being detected. Lysing or releasing agents capable of releasing the toxins from the bacteria may adversely effect the structure of the toxins such that the toxins can not be recognized. There exists a need for better and more accurate assays for Shiga-like toxins. A simple and sensitive assay useful, for example, on stool samples could eliminate the need for tissue culture assays or serological testing and would satisfy a longfelt clinical need.

SUMMARY OF THE INVENTION

The present invention pertains to a rapid method for detecting virulence-associated factors of bacterial origin in samples suspected of containing the factors. The method is particularly useful for detecting bacterial toxins such as bacterial toxins from the Shiga family. Toxins from the Shiga family have been associated with prolonged bloody diarrhea, hemolytic uremic syndrome and thrombotic thrombocytopenic purpura. A method useful for detecting these toxins would provide valuable information necessary to diagnose the aforementioned conditions or diseases. The virulence-associated factors (toxins) can be detected directly from a stool sample. The method of the present invention is not labor intensive like conventional cell culture assays and further does not require highly skilled personnel.

The present invention pertains to a method for detecting at least one virulence-associated factor (hereinafter VAF) in a sample. The sample suspected of containing the VAF-producing bacteria is contacted with a VAF releasing solution under conditions which releases VAF from the bacteria. The released VAF subsequently is immunochemically detected. The preferred method is a membrane-based enzyme linked immunosorbent assay for immunochemically detecting the well-characterized Shiga family toxins including SLT I and SLT II.

The present invention also pertains to the VAF releasing solution containing a variety of components each added for its ability to impart a desired property to the overall solution. The VAF releasing solution may be used in the method described above and further may be used in other methods requiring release of a VAF from bacteria. The components of the solution include a surface active agent, an immunological enhancing agent and an antibiotic. The solution also may contain an enzyme inhibitor and other components which would impart favorable properties to the overall solution. The components of the solution are all combined in a buffered solution having a pH appropriate for the solution's intended function.

The present invention also pertains to kits containing the reagents necessary to conduct the methods described herein. The invention even further pertains to components of a device, e.g. a combination of a membrane and a P1 antigen, used to conduct the described methods.

DETAILED DESCRIPTION

Figure 1:
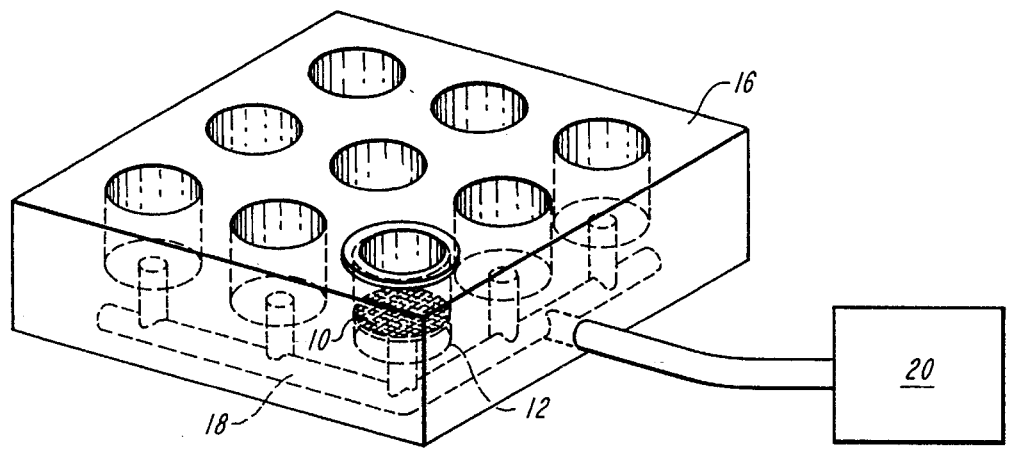
FIG. 1 depicts a device used in a membrane based enzyme-linked immunosorbent assay.

The present invention pertains to a method for immunochemically detecting at least one virulence-associated factor (VAF) in a sample. The method involves contacting a sample containing a VAF-producing bacteria with a VAF releasing solution under conditions which release the VAF(s) from the bacteria. The method further involves immunochemically detecting the released VAF in the sample. The VAF releasing solution is a buffered solution containing at least one surface active agent and the solution releases the VAFs without impeding the immunochemical detectability of the VAFs.

The term "virulence-associated factor" is intended to include molecules associated or involved in the virulence or pathogenicity of bacteria. Virulence-associated factors are well known in the art and are described by Hale (*Microbiological Reviews*, June 1991, p. 206–224) and Janda (*Clinical Microbiology Reviews*, October 1991, p. 397–410), the contents of both references are hereby incorporated by reference. Examples of virulence-associated factors include such molecules as bacterial toxins, adhesive factors and heat release proteins. Some virulence-associated factors which may be detected using the method of the present invention are as follows (the factors are followed by their respective enteric pathogen in parentheses): Shiga-like toxin I, Shiga-like toxin II, other toxins of the Shiga family, heat-labile enterotoxin, heat-stable enterotoxins a+b, heat stable-like enterotoxins, adhesins, lipopolysaccharide-0157 antigen, hemolysin (*E. coli*); cholera toxin, flagella, zot toxin (*V. cholerae*); Shiga toxin (*Shigella dysenteriae*); toxin A, toxin B (*C. difficile*); surface antigen for invasion (Shigella dysenteriae; invasive *E. coli*); heat release protein (*Yersinia enterocolitica*); cytotoxin(s), hemolysin, enterotoxin, proteases, siderophores, invasins, outer membrane protein, pili, LPS, flagella (Aeromonas spp.); enterotoxin, adhesion factors, flagella (Campylebacter spp.); LPS (Salmonella spp.) and surface antigens from enteric parasites and viruses. The above list is not intended to be inclusive of all useful VAFs and is merely provided to illustrate examples of such factors. The most common VAFs of the present invention are bacterial toxins.

The term "bacterial toxin" is intended to include various toxins produced by bacteria. The preferred bacterial toxins are those toxins which are located close to the cell wall of the bacteria, e.g. located in the periplasmic space, such that the toxins may be released without actually dissolving the entire cell membrane. Examples of such toxins include Shiga family toxins, LT enterotoxins and ST enterotoxins.

The term "Shiga family toxins" is intended to include Shiga toxin and other toxins which are structurally and/or functionally similar to the Shiga toxin, e.g. have the A and B moieties described above. "Structurally similar" is intended to include toxins which have the same or similar core structure differing in individual amino acid substitutions. Functionally similar is intended to include toxins which share the same or similar function. Presently, SLT I and SLT II are well characterized Shiga-like toxins.

Bacteria which can be assayed with this invention include bacteria which are capable of producing VAFs. Bacteria which are known to produce the preferred VAFs which are toxins within the Shiga family include *Escherichia coli, Vibrio Cholerae, Shigella dysenteriae* Type I, and other species of the genus Shigella. The bacteria which is most commonly detected as a producer of SLT I and SLT II is *E. coli* serotype 0157:H7.

Samples which may be used within the present invention include samples suspected of containing a bacterial VAF desired to be detected. Samples include biological samples such as blood, portions of blood, urine, or stool. The preferred biological sample is stool. The sample also may be a food product. The sample may be used directly or may be used as a suspension. For example, it may be suspended in a buffered solution. Microorganisms producing Shiga-like toxins have been known to contaminate beef from dairy cows, milk and other meat products. These samples could be used directly or could be pretreated prior to being tested for the toxin. It should be understood that the pretreatment steps would vary depending on the sample being utilized and the VAFs desired to be detected. For example, it may be appropriate to cut a meat product into pieces or to chemically treat (e.g. enzymatically) or include a broth enrichment of the meat sample prior to use in the method of this invention.

The term "immunochemically detecting" is intended to include methods of detection which rely upon the use of immunological materials, e.g. antibodies, antigens, or combinations thereof. Examples of immunoassays which can be used to immunochemically detect VAFs, e.g., bacterial toxin(s), include enzyme-linked immunosorbent assay (ELISA), immunoblot assays, and immunoagglutination assays. Such immunoassays are well known in the art.

One preferred immunoassay useful to immunochemically detect VAFs of the present invention is the so called enzyme-linked immunosorbent assay (ELISA) (See Ausubel et al., *Current Protocols in Molecular Biology*, Volume 2 Section 11 (1992), the contents of which are hereby incorporated by reference.) The most preferred immunoassay is a membrane-based ELISA using a device having an antigen immobilized on a membrane. The antigen-membrane combination is situated in a well allowing reagents to be contained by the well when in contact with the antigen-membrane combination.

Figure 2:
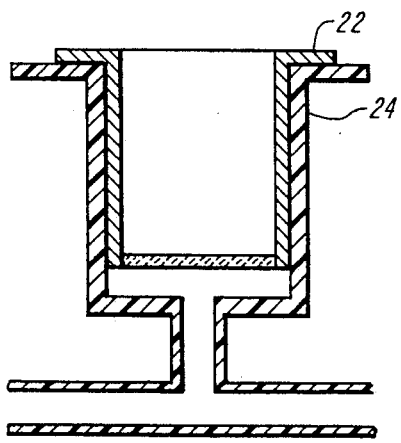
FIG. 2 is a cross-sectional view of a single well in the plate depicted in FIG. 1 containing a suspended membrane.

As shown in FIGS. 1 and 2, the device 10 has an antigen 11 immobilized on a membrane 12. The antigen-membrane combination is located in a well 14 which preferably is part of a multi-well plate 16. The plate 16 contains a plurality of wells 14 arranged in communication with conduits 18 for removing fluids from the wells 14 using a removal means 20, e.g., a vacuum source. The removal means 20 typically has a reservoir for holding the aspirated waste solutions. FIG. 2 is a cross-sectional view of a single well 14 in plate 16 depicting the membrane 12 suspended in the well 14 using a holder 21. The holder 21 is constructed and arranged to fit securely within the well 14 and preferably has a flange 22 extending about its periphery. The flange 22 provides the user with a gripping surface allowing the membrane 12 to be removably placed in the well 14. Alternatively, the membrane 12 can be permanently fixed within the well 14. Various other designs will be apparent to one skilled artisan. An example of a commercially-available device which may be used in this invention is a Capsure Vac device (sold by Stratocon Diagnostics Int'l of Norwell, Mass.).

The method of this invention will be further illustrated using SLT I and SLT II as the VAFs. The immobilized antigen (P1 antigen) on the membrane is contacted with a sample suspected of containing SLT I and/or SLT II under conditions which allow the SLT I and SLT II to bind the antigen forming an antigen-toxin complex. The bound complex is subsequently contacted with a labelled antibody reactive towards the toxin(s). The presence or absence of the label is detected as an indication of the presence or absence of SLT I and/or SLT II.

It is known that the B chain is the receptor-binding moiety for Shiga family toxins. This chain recognizes cell-surface glycolipids with a terminal $\alpha$-D,Galp-(1-4)-D-Galp disaccharide portion. Antigens containing this terminal portion would be useful in this invention. An example of such an antigen is a $P_1$ blood group antigen. The $P_1$ antigen is derived from human erythrocytes and it forms part of the P blood group system.

It should be understood that an agent other than an antigen may be immobilized on the membrane used in the membrane-based ELISA. The agent may be any immunoreactive capture material capable of binding to the respective VAFs. For example, a cocktail of two antibodies may be used in place of the antigen wherein one of the antibodies is reactive with a first VAF (SLT I) and the second antibody is reactive with a second VAF (SLT II). Another possibility may be the use of a bifunctional antibody reactive towards both VAFs.

The conditions which allow the VAFs, e.g., SLT I and SLT II, to bind to their respective antigens forming an antigen-VAF complex are conditions such as temperature and incubation time. One skilled in the art can readily adjust these conditions to allow the binding to occur. For example, the antigen can be incubated with the sample suspected of containing the VAFs for a time period in the range of about fifteen minutes to about twenty four hours, more preferably about thirty minutes to about two hours, most preferably about one hour. The incubation can be conducted at a temperature in the range of about room temperature to 45° C., more preferably room temperature to about 37° C., and most preferably about room temperature. The incubation further can be conducted in the presence of humidity.

It should be understood that the labelled antibody reactive towards each VAF or toxin may be a single antibody or may be more than one antibody as described in the examples below. For example, the labelled antibody may be a combination of a first polyclonal antibody reactive towards the VAFs or toxins followed by a labelled monoclonal antibody reactive with the antibody type of the first antibody. The labelling antibodies also could be monoclonal and/or polyclonal antibodies. Appropriate labels for the antibodies are well known in the art and any label capable of being detected in the particular assay may be used. Examples of labels which may be used include enzymatic, fluorescent, and radioisotopic labels.

The method of the present invention may be used not only to detect the presence or absence of a particular VAF but also to quantitate the amount of VAF in a sample, if desired. For example, if the method is used to detect the presence or absence of a particular VAF, the user would only have to observe whether or not the reaction for a particular label has occurred, e.g., a color change for an enzymatic label. If the user is interested in the quantity of VAF, then the actual absorbance of a color change can be measured and compared to a curve of known standards or VAFs.

An advantage of the method of the present invention is that it can rapidly detect VAFs. Rapid detection is intended to include detection in less than about four hours, more preferably less than about two hours, most preferably less than about thirty minutes. It should be understood that the time of the detection method will vary depending on the reagents selected for use in the method. For example, if a combination of two antibodies is used as the labelled immunoreactive material then the method would be somewhat longer than if a single labelled antibody were used.

Another aspect of the present invention is the VAF releasing solution. The VAF releasing solution may be used in the method described above and further may be used in any assay requiring the release of a VAF from bacteria. The solution is capable of releasing a VAF from bacteria in a form which does not impede the immunochemical detectability of the VAF. In one embodiment, the VAF releasing solution includes at least one surface active agent, an immunological enhancing agent, and an antibiotic. The VAF releasing solution further may comprise an enzyme inhibitor. The components of the VAF releasing solution preferably are buffered to a pH in the range of about 7 to about 9, more preferably, in the range of about 7.2 to about 8.0, most preferably about 7.4 to about 7.8. Two illustrative buffers useful in maintaining the desired pH range are Tris-HCl, CHAPs buffer (sold by Pierce Chemical Co., Rockford, Ill.), and carbonate buffers. Any buffers compatible with the VAF-producing bacteria and which do not detrimentally effect the other reagents in the solution may be used.

The surface active agent is an agent capable of releasing the VAF from the bacteria in a manner that does not significantly affect the structure of the VAF or detrimentally affect or impede its immunochemical detectability. Examples of such agents include N,N', N'-polyoxyethylene (10)-N-Tallow-1,3-diaminopropane (sold as EDT-20 by Sigma Chemical, St. Louis, Mo.), sulfubetaine derivatives of cholic acid (sold as CHAPs by Pierce Chemical Co., Rockford, Ill.), alkyl glucosides, e.g., octyl-B-glucoside, polyoxyethylenesorbitan monolaurate (sold as Tween 20 by Sigma Chemical) and octylphenolethylene oxide condensate (average of 9.0 moles of ethylene per mole of phenol) (sold as Nonidet® P-40 by Sigma Chemical). One preferred surface active agent is N,N',N'-polyoxyethylene (10)-N-Tallow-1,3-diaminopropane which has the following physical properties and structural formula:

$$\begin{array}{c} (CH_2CH_2O)_xH \qquad\qquad (CH_2CH_2O)_yH \\ | \qquad\qquad\qquad\qquad\qquad | \\ R-N-CH_2-CH_2-CH_2\cdots N \\ | \\ (CH_2CH_2O)_zH \end{array}$$

where $R = $ a $C_{12}$ to $C_{18}$ tallow group and $x+y+z=10$

This surface active agent is a clear liquid having a moisture content of 1%. The specific gravity of the surface active agent is 0.99 at 25° C. It has a typical molecular weight of 780 mw including 10 moles of ethylene oxide. Other physical properties of the preferred surface active agent include a flash point (Pensky-Martens method) of 510 degrees F, a surface tension of a 0.1% solution of 38.2 dynes/cm, and a surface tension of a 1.0% solution of 38.3 dynes/cm.

The concentration of the surface active agent in the solution is selected such that the surface active agent is present at an amount which allows it to perform its intended function of aiding in the release of the VAF from the bacteria. The preferred concentration range is from about $5 \times 10^{-7}$ to about 1.0 percent, more preferably about $5 \times 10^{-5}$ to about 0.5 percent, and most preferably $1.0 \times 10^{-4}$ to about $1.0 \times 10^{-2}$ percent. All of the concentrations are volume percentages based on the VAF releasing solution.

Surface active agents which are particularly desirable for use in the method of the present invention may be selected by using the "wetting assay" described in detail in Example 6. Surface active agents which perform similar to EDT-20 in the wetting assay share the same or similar wetting ability as EDT-20 and therefore would be useful in the VAF releasing solution. For example, Tween 20 and Nonidet P40 performed similarly to EDT-20 in the wetting assay. The preferred surface active agents are within about fifty drops of EDT-20 based upon the described wetting assay, more preferred within twenty drops, most preferred within 10 drops.

The immunological enhancing agent is an agent capable of enhancing the VAF release and/or detectability. The agent further may stabilize the VAF in its immunochemically detectable form after its release. For example, the agent may stabilize the three dimensional conformation of the VAF such that its binding partner is more reactive towards it. An example of an immunological enhancing agent is urea. The concentration of the immunological enhancing agent in the solution is selected such that the enhancing agent is present at an amount allowing it to enhance the VAF release and/or detectability. The preferred concentration range is from about 0.1M to about 15M, more preferably from about 1M to about 10M, and most preferably about 8M, based on a final concentration in the VAF releasing solution.

Antibiotics are well known in the art and can be included in the VAF releasing solution to aid in the disruption of the bacteria and leakage of the VAF(s). Examples of antibiotics include polymyxin nonapeptides, polymyxins and salts thereof, e.g. polymyxin B sulphate, polymyxin B, and mytomycin-C. The concentration of the antibiotic in the solution is selected to allow the antibiotic to be present at an amount sufficient for it to perform its intended function. The preferred concentration range is from about $5.0 \times 10^{-6}$ to about 1.0, more preferably from about $5.0 \times 10^{-3}$ to about 0.5, most preferably about 0.05 to about 0.1. All of these concentrations are based upon mg of antibiotic/ml of VAF releasing solution.

Enzyme inhibitors are agents capable of inhibiting enzymes, e.g., proteases such as trypsin, from acting on the VAF which are being released and detected. Examples of enzyme inhibitors include protease and trypsin inhibitors, e.g., phenylmethylsulphonyl fluoride. The concentration of the enzyme inhibitor is selected such that the enzyme inhibitor is present at an amount allowing it to inhibit enzymes from degrading the VAFs prior to their detection. The preferred concentration range is from about $1.0 \times 10^{-3}$ µg/ml to about 1 mg/ml, more preferred from about 0.01 µg/ml to about 100 µg/ml, and most preferably about 0.1 mg/ml to 10 µg/ml. All of the concentrations are based upon mg of inhibitor per ml of VAF releasing solution.

It should be understood that the VAF releasing solution may contain additional reagents which enhance the release and/or detectability of the VAF in the sample or impart other favorable properties to the overall solution. These additional reagents may include preservatives, whole serum and serum components, e.g. serum albumins.

Figure 3:
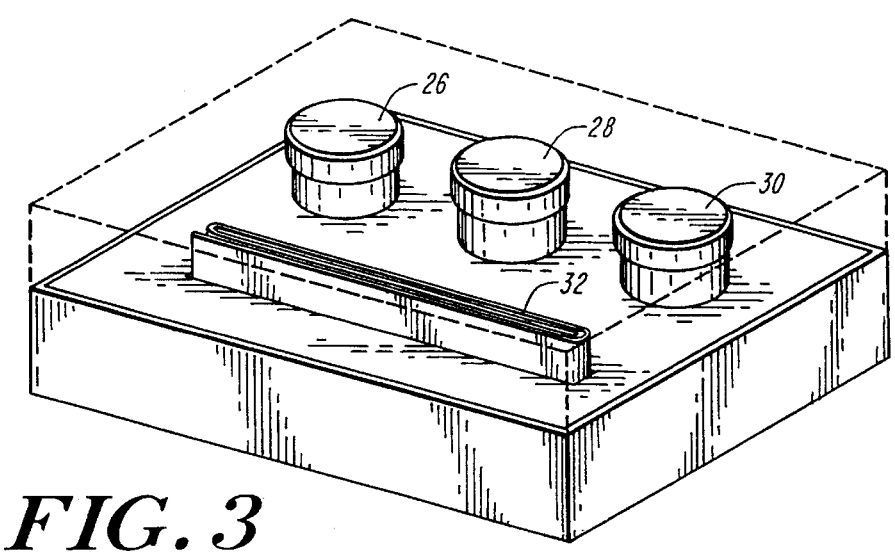
FIG. 3 depicts a kit useful for detecting a bacterial virulence-associated factor in a sample.

The present invention also pertains to kits which are useful for carrying out the above-described methods for detecting the presence or absence of a bacterial VAF in a sample. As shown in FIG. 3, the kit includes a first container 26 of a VAF-releasing solution as described above, a second container 28 of a capture immunoreactive material reactive with the VAF, a third container 30 of a labelled immunoreactive material reactive with the VAF, and optionally instructions 32 for using the VAF releasing solution and immunoreactive materials in a method for immunochemically detecting the VAF. The capture immunoreactive material may be any material capable of binding to the VAF being detected. For example, if the toxin desired to be detected is a Shiga family toxin, the capture immunoreactive material may include a P1 antigen. The labelled immunoreactive material may be a labelled single antibody or a combination of antibodies as described above.

The following examples are provided to further illustrate the above-described invention and are not intended to be further limiting in any way.

Example 1

Preparation of the Virulence-Associated Factor Releasing Solution

Virulence-associated factor-releasing solution is prepared to include 8M urea (Molecular Biology Reagent Grade, Sigma Chemical Company, St. Louis, Mo.), polymyxin B sulphate (0.1 mg/ml) (Sigma Chemical Company, potency equals 7,900 U/mg), N,N',N'-polyoxyethylene (10)-N-Tallow-1,3-diaminopropane (sold as EDT-20, Sigma Chemical Company, 100% solution diluted 1:200,000), phenylmethylsulphonyl fluoride (1 mM) (Sigma Chemical Company, St. Louis, Mo.). The above reagents are dissolved to the appropriate final concentrations in 10 mM Tris HCl (Sigma Chemical Company, St. Louis, Mo.) and 150 mM NaCl (pH=7.6).

Example 2

ELISA Method for Detecting SLT I or SLT II in Bacterial Suspensions

The following reagents are referred to throughout the examples and their components are set forth below:

| Reagents | | | |
|---|---|---|---|
| a. | Sodium carbonate buffer: | | |
| | Na2CO3 | 1.59 g | |
| | NaHCO3 | 2.93 g | |
| | NaN3 | 0.2 g | |
| | distilled water | 1000 ml | pH 9.6 |
| b. | Tris buffered saline (TBS): | | |
| | Tris-Cl | 50 mM | |
| | NaCl | 150 mM | |
| | distilled water | 1000 ml | pH 7.6 |
| c. | Blocking solution: | | |
| | TBS with 5% non-fat milk | | |
| d. | Wash solution/diluent: | | |
| | TBS with 0.05% Tween 20 | | |
| e. | VAF release solution: | | |
| | 8M urea | | |
| | 1:200,000 EDT-20 | | |
| | 0.1 mg/ml Polymyxin B | | |
| | TBS | | |

Nitrocellulose membranes are inserted in Capsure Vac formats (Stratocan Diagnostics Int'l., Norwell, Mass.) and wet with distilled water. P1 antigen solution (provided by Dr. Arthur Donahue-Rolf, Division of Geographic Medicine, New England Medical Center, Tufts University, Boston, Mass.) (100 µl of 1 µg/ml of carbonate buffer) is placed on the nitrocellulose membrane and incubated for one hour at 37° C. The vacuum line is activated and any remaining liquid is drawn through the membrane. Subsequently, a solution of 5% non-fat milk in Tris-buffered saline (hereinafter blocking solution) (100 µl) having a pH of 7.6 is added to the nitrocellulose membrane and incubated at 37° C. with humidity for fifteen minutes.

Several bacterial colonies suspected of producing SLT I and II are scraped and suspended in 500 µl of the virulence-associated factor releasing solution described in Example 1. An aliquot (100 µl) of this suspension is then applied to the nitrocellulose membrane and incubated at 37° C. for one hour. The membrane coated with the applied materials is washed four times with Tris buffered saline (TBS) pH=7.6, containing 0.05% Tween-20. Subsequent to the washing step, rabbit polyclonal anti-SLT I and SLT II sera (also provided by Dr. Arthur Donahue-Rolf) is diluted 1:5,000 in the blocking solution and is added to the washed membrane and incubated for fifteen minutes at 37° C. A second washing step is carried out as described above. Goat anti-rabbit IgG-biotinylated conjugate obtained from Pierce Chemicals as part of Pierce's Immuno Pure ABC alkaline phosphatase rabbit IgG staining kit is diluted by adding one drop to 10 ml of blocking solution and 100 µl of this solution is added to the washed membrane and incubated for thirty minutes at room temperature. A third washing step is carried out as described above. A staining reagent is prepared previously by adding two drops of each of the reagents A and B (the Pierce ImmunoPure kit identified above) to 10 ml of wash solution and allowing it to stand for at least thirty minutes. An aliquot (100 µl) of this staining reagent is added to each well and incubated for thirty minutes. The liquid is drawn through the membrane and a washing step is carried out as described above. The enzyme's substrate (100 µl) of alkaline phosphatase conjugate substrate reagents (BioRad Laboratories, Richmond, Calif.) is added to the washed membrane and incubated for five minutes at room temperature. The membrane is washed with distilled water and the blue color remains on the membrane if SLT I or SLT II is present in the sample.

EXAMPLE 3

ELISA Method for Detecting SLT I or SLT II in Bacterial Pellets Obtained from An Overnight Broth Nitrocellulose membranes are inserted in Capsure Vac wells (Stratocan Diagnostics Int'l., Norwell, Mass.) and wet with distilled water. P1 antigen solution (provided by Dr. Arthur Donahue-Rolf, Division of Geographic Medicine, New England Medical Center, Tufts University, Boston, Mass.) (100 µl of 1 µg/ml of carbonate buffer) is placed on the nitrocellulose membrane and incubated for one hour at 37° C. The vacuum line is activated and any remaining liquid is drawn through the membrane. Subsequently, a solution of 5% non-fat milk in Tris-buffered saline (hereinafter the "blocking solution") (100 µl) having a pH of 7.6 is added to the nitrocellulose membrane and incubated at 37° C. with humidity for fifteen minutes.

Bacteria suspected of producing SLT I and SLT II are inoculated into 5.0 ml of Trypticase soy broth and incubated with aeration overnight at 37° C. The culture broth is centrifuged (3,800 g) for twenty minutes and the supernatant discarded. The pellet is resuspended in 200 μl of VAF release buffer and incubated for one hour at 37° C. This sample is centrifuged (12,000 g) for two minutes and the supernatant is saved. An aliquot (100 μl) of the supernatant is then applied to the nitrocellulose membrane and incubated at 37° C. for one hour. The membrane coated with the applied materials is washed four times with Tris buffered saline (TBS) pH=7.6, containing 0.05% Tween-20. Subsequent to the washing step, rabbit polyclonal anti-SLT I and SLT II sera (also provided by Dr. Arthur Donahue-Rolf) is diluted 1:5,000 in the blocking solution and is added to the washed membrane and incubated for fifteen minutes at 37° C. A second washing step is carried out as described above. Goat anti-rabbit IgG-biotinylated conjugate obtained from Pierce Chemicals as part of Pierce's Immuno Pure ABC Alkaline phosphatase rabbit IgG staining kit is diluted by adding one drop to 10 ml of blocking solution and 100 μl of this solution is added to the washed membrane and incubated for thirty minutes at room temperature. A third washing step is carried out as described above. A staining reagent is prepared previously by adding two drops of each of the reagents A and B (from the Pierce ImmunoPure kit identified above) to 10 ml of wash solution and allowing it to stand for at least thirty minutes. An aliquot (100 μl) of this staining reagent is added to each well and incubated for thirty minutes. The liquid is drawn through the membrane and a washing step is carried out as described above. The enzyme's substrate (100 μl of alkaline phosphatase conjugate substrate reagents (BioRad Laboratories, Richmond, Calif.)) is added to the washed membrane and incubated for five minutes at room temperature. The membrane is washed with distilled water and the blue color remains on the membrane if SLT I or SLT II is present in the sample.

EXAMPLE 4

ELISA Method for Detecting SLT I or SLT II Producing *E. coli* in Processed Hamburger.

Nitrocellulose membranes are inserted in Capsure Vac formats (Stratocan Diagnostics Int'l., Norwell, Mass.) and wet with distilled water. P1 antigen solution as described above (100 µl of 1 µg/ml of carbonate buffer) is placed on the nitrocellulose membrane and incubated for one hour at 37° C. The vacuum line is activated and any remaining liquid is drawn through the membrane. Subsequently, a solution of 5% non-fat milk in Tris-buffered saline (hereinafter blocking solution) (100 µl) having a pH of 7.6 is added to the nitrocellulose membrane and incubated at 37° C. with humidity for fifteen minutes.

Processed hamburger (a pea sized amount—approximately 100 mg) is placed in 5.0 ml of Tryticase soy broth and incubated with aeration for three hours at 37° C. The culture broth is centrifuged (2000 ×g) for two minutes and the supernatant is saved for a second centrifugation step. The supernatant is centrifuged (12,000×g) for two minutes and the supernatant is discarded. The pellet is suspended in 400 µl of the VAF releasing solution described in Example 1 along with 0.5% fetal bovine serum. This is incubated for one hour at 37° C. The suspension is mixed thoroughly and centrifuged. An aliquot (100 µl) of the supernatant is then applied to the nitrocellulose membrane and incubated at 37° C. for one hour. The membrane coated with the applied materials is washed four times with Tris buffered saline (TBS) pH=7.6, containing 0.05% Tween-20. Subsequent to the washing step, rabbit polyclonal anti-SLT I and SLT II sera (also provided by Dr. Arthur Donahue-Rolf) is diluted 1:5,000 in the blocking solution and is added to the washed membrane and incubated for fifteen minutes at 37° C. A second washing step is carried out as described above. Goat anti-rabbit IgG-biotinylated conjugate obtained from Pierce Chemicals as part of Pierce's Immuno Pure ABC Alkaline phosphatase rabbit IgG staining kit is diluted by adding one drop to 10 ml of blocking solution and 100 µl of this solution is added to the washed membrane and incubated for thirty minutes at room temperature. A third washing step is carried out as described above. A staining reagent is prepared previously by adding two drops of each of the reagents A and B (from the Pierce ImmunoPure kit identified above) to 10 ml of wash solution and allowing it to stand for at least thirty minutes. An aliquot (100 µl) of this staining reagent is added to each well and incubated for thirty minutes. The liquid is drawn through the membrane and a washing step is carried out as described above. The enzyme's substrate (100 µl alkaline phosphatase conjugate substrate reagents (BioRad Laboratories, Richmond, Calif.)) is added to the washed membrane and incubated for five minutes at room temperature. The membrane is washed with distilled water and the blue color remains on the membrane if SLT I or SLT II is present in the sample.

EXAMPLE 5

ELISA Method for Detecting SLT I or SLT II In a Stool Specimen Containing SLT-Producing E. Coli.

Nitrocellulose membranes were inserted in Capsure Vac formats (Stratocan Diagnostics Int'l., Norwell, Mass.) and wet with distilled water. P1 antigen solution as described above (100 µl of 1 µg/ml of carbonate buffer) was placed on the nitrocellulose membrane and incubated for one hour at 37° C. The vacuum line was activated and any remaining liquid was drawn through the membrane. Subsequently, a solution of 5% non-fat milk in Tris-buffered saline (hereinafter blocking solution) (100 µl) having a pH of 7.6 was added to the nitrocellulose membrane and incubated at 37° C. with humidity for fifteen minutes.

A stool specimen (100 mg) mixed with $10^8$ CFU of SLT producing E. coli. was combined with 400 µl of VAF releasing solution containing 0.5% fetal bovine serum. This mixture was incubated for one hour at 37° C. The same procedure was used for positive (purified SLT) and negative (diluent) controls. The mixtures were centrifuged (12000×g) for five minutes and the supernatant was saved. An aliquot (100 µl) of the supernatant from each mixture (stool and controls) was then applied to the nitrocellulose membrane and incubated at 37° C. for one hour. The membrane coated with the applied materials was washed four times with Tris buffered saline (TBS) pH=7.6, containing 0.05% Tween-20. Subsequent to the washing step, rabbit polyclonal anti-SLT I and SLT II sera (also provided by Dr. Arthur Donahue-Rolf) was diluted 1:5,000 in the blocking solution and was added to the washed membrane and incubated for fifteen minutes at 37° C. A second washing step was carried out as described above. Goat anti-rabbit IgG-biotinylated conjugate obtained from Pierce Chemicals as part of Pierce's Immuno Pure ABC Alkaline phosphatase rabbit IgG staining kit was diluted by adding one drop to 10 ml of blocking solution and 100 µl of this solution was added to the washed membrane and incubated for thirty minutes at room temperature. A third washing step was carried out as described above. A staining reagent was prepared previously by adding two drops of each of the reagents A and B (from the Pierce ImmunoPure kit identified above) to 10 ml of wash solution and allowed to stand for at least thirty minutes. An aliquot (100 µl) of this staining reagent was added to each well and incubated for thirty minutes. The liquid was drawn through the membrane and a washing step was carried out as described above. The enzyme's substrate (100 µl of alkaline phosphatase conjugate substrate reagents (BioRad Laboratories)) was added to the washed membrane and incubated for five minutes at room temperature. The membrane was washed with distilled water. A dark purplish, blue color appeared on the membranes holding the stool specimen containing the E. coli and the positive control. The membrane holding the negative control appeared white in color.

EXAMPLE 6

An Assay for Measuring the Wetting Ability of Surface Active Agents

Distilled water (100 ml) was placed in a beaker and a flat, thin, plastic disc was placed in the beaker and allowed to float on the surface of the water. Five surface active agents were selected and 1% solutions of each agent in distilled water were prepared. The solutions were added dropwise to the distilled water in beaker and the wetting index of the respective surface active agents was calculated by counting the number of drops of the solution which were required to sink the plastic disc. Tween 20 and Nonindet P-40 exhibited a "wetting index" quote similar to EDT-20 and the results are set forth in Table 1 below:

TABLE 1

| Surface Active Agent | Drops (100 ul) (Number of Drops (100 ul) Required to Sink Disc) | |
| --- | --- | --- |
| Triton X-100 | 18 | av. 20 |
| | 24 | |
| | 18 | |
| Nonidet P-40 | 58 | av. 61 |
| | 90 | |
| | 94 | |
| Tween-20 | 86 | av. 101 |
| | 101 | |
| | 115 | |

TABLE 1-continued

| Surface Active Agent | Drops (100 ul) (Number of Drops (100 ul) Required to Sink Disc) | |
|---|---|---|
| SDS | 168 | av. 188 |
|  | 213 |  |
|  | 184 |  |
| EDT-20 | 98 | av. 95 |
|  | 92 |  |
|  | 95 |  |

By the above-described wetting ability test, surfactants useful in the present invention will typically have a wetting index from about 50 to 150.

Those skilled in the art will be able to ascertain, using no more than routine experimentation, many equivalents of the specific embodiments of the invention described herein.

These and all other equivalents are intended to be encompassed by the following claims.

I claim:

1. A method for immunochemically detecting a virulence-associated factor in feces, comprising:

contacting a feces sample suspected of containing a virulence-associated factor producing bacteria with a factor releasing solution under conditions which release at least one virulence-associated factor from the bacteria; and immunochemically detecting the presence or quantity of the released virulence-associated factor, wherein said virulence-associated factor is selected from the group consisting of a bacterial toxin, a surface antigen, an adhesive factor, and a heat-release protein;

said factor releasing solution containing:

a) a surface-active agent;
b) urea; and
c) an antibiotic selected from the group consisting of polymyxins and mitomycin C; and said solution releasing the virulence-associated factor without impeding the immunochemical detectability of the virulence-associated factor.

2. A method as claimed in claim 1 wherein the virulence-associated factor is a bacterial toxin.

3. A method as claimed in claim 1 wherein the at least one virulence-associated factor in the contacting step is selected from the group consisting of Shiga-like toxin I, Shiga-like toxin II, heat-labile enterotoxin, heat stable enterotoxins a+b, heat stable-like enterotoxins, adhesins, lipopolysaccharide-0157 antigen, hemolysin, cholera toxin, flagella, zot toxin, Shiga toxin, toxin A, toxin B, surface antigen for invasion, cytotoxins, proteases, siderophores, invasins, outer membrane protein, pili, and lipopolysaccharide.

4. A method as claimed in claim 1 wherein the bacterial toxin is Shiga-like toxin I or Shiga-like toxin II.

5. A method as claimed in claim 1 wherein the bacterial toxin includes a mixture of Shiga-like toxin I and Shiga-like toxin II.

6. A method as claimed in claim 1 wherein the antibiotic is polymyxin B sulphate.

7. A method as claimed in claim 1 wherein the virulence-associated factor releasing solution in the contacting step further comprises a protease inhibitor.

8. A method as claimed in claim 1 wherein the surface active agent in the virulence-associated factor releasing solution is selected from the group consisting of N,N',N'-polyoxyethylene(10)-N-tallow-1,3-diaminopropane, sulfobetaine derivatives of cholic acid, alkyl glucosides, polyoxyethylenesorbitan monolaurate and octylphenolethylene oxide condensate.

9. A method as claimed in claim 8 wherein the surface active agent is N,N',N'-polyoxyethylene(10)-N-tallow-1,3-diaminopropane.

10. A method as claimed in claim 1 wherein said surface-active agent comprises N,N',N'-polyoxyethylene(10)-N-tallow-1,3-diaminopropane, and said antibiotic comprises polymyxin B sulphate.

11. A method as claimed in claim 1 wherein the virulence-associated factor is immunochemically detected by an enzyme-linked immunosorbent assay.

12. A method as claimed in claim 1 wherein the contacting and immunochemically detecting steps are completed in a time span of less than about four hours.

13. A method as claimed in claim 12 wherein the contacting and immunochemically detecting steps are completed in a time span of less than about two hours.

14. A method as claimed in claim 13 wherein the contacting and immunochemically detecting steps are completed in a time span of less than about thirty minutes.

15. A method as claimed in claim 1 wherein the presence of at least one virulence-associated factor is detected in the immunochemically detecting step.

16. A method as claimed in claim 1 wherein the quantity of at least one virulence-associated factor is detected in the immunochemically detecting step.

17. A method for detecting a Shiga-like toxin directly from a stool sample, comprising:

contacting a stool sample suspected of containing bacteria producing at least one Shiga-like toxin with a toxin releasing solution under conditions such that at least one Shiga-like toxin is released; and immunochemically detecting any of the at least one Shiga-like toxin released directly from bacteria in the stool sample by the toxin releasing solution.

18. A method as claimed in claim 17 wherein the at least one Shiga-like toxin in the contacting step includes a mixture of both Shiga-like toxin I and Shiga-like toxin II.

19. A method as claimed in claim 17 wherein the immunochemically detecting step is an enzyme-linked immunosorbent assay step.

20. A method as claimed in claim 19 wherein the enzyme-linked immunosorbent assay step is membrane-based.

21. A method for immunochemically detecting Shiga-like toxin I or Shiga-like toxin II in feces, comprising:

contacting a feces sample suspected of containing Shiga-like toxin I or Shiga-like toxin II producing bacteria with a toxin releasing solution under conditions which release Shiga-like toxin I or Shiga-like toxin II from the bacteria; and immunochemically detecting the presence or quantity of the released Shiga-like toxin I or Shiga-like toxin II, said toxin releasing solution containing:

a) a surface active agent selected from the group consisting of N,N',N'-polyoxyethylene(10)-N-tallow-1,3-diaminopropane, polyoxyethylenesorbitan monolaurate, and octylphenolethylene oxide condensate;
b) urea;
c) a polymyxin; and
d) phenylmethylsulphonyl fluoride and said solution releasing the Shiga-like toxin I or Shiga-like toxin II without impeding the immunochemical detectability of the Shiga-like toxin I or Shiga-like toxin II.

* * * * *